United States Patent
Shinozaki et al.

(10) Patent No.: US 6,506,815 B2
(45) Date of Patent: Jan. 14, 2003

(54) RESIN COMPOSITION FOR DENTURE BASE

(75) Inventors: Yutaka Shinozaki, Tokyo (JP); Tomohiro Kumagai, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/948,663

(22) Filed: Sep. 10, 2001

(65) Prior Publication Data

US 2002/0065338 A1 May 30, 2002

(30) Foreign Application Priority Data

Sep. 26, 2000 (JP) .................................... 2000-292310

(51) Int. Cl.⁷ .............................. C08F 2/48; C08F 2/50; A61C 13/01
(52) U.S. Cl. ............................ 522/74; 522/71; 522/79; 522/81; 522/83; 522/178; 522/179; 522/96; 522/90; 522/182; 522/120; 522/908; 522/28; 522/60; 522/62; 522/38; 522/64; 433/228.1; 433/168.1; 433/167; 523/109; 523/115; 523/120
(58) Field of Search ................................ 523/120, 115, 523/109; 522/120, 28, 908, 60, 62, 38, 64, 178, 179, 182, 96, 90, 71, 74, 79, 81, 83; 433/228.1, 168.1, 167

(56) References Cited

U.S. PATENT DOCUMENTS 4,782,100 A * 11/1988 Iwamoto et al. ............. 522/120
5,155,252 A * 10/1992 Yamamoto et al. .......... 560/190
5,663,214 A *  9/1997 Okada ......................... 523/120
5,698,611 A * 12/1997 Okada et al. ................ 522/120

FOREIGN PATENT DOCUMENTS

WO         86/05793         * 10/1986

* cited by examiner

Primary Examiner—James J. Seidleck
Assistant Examiner—Sanza L. McClendon
(74) Attorney, Agent, or Firm—Oblon, Spivak, McClelland, Maier & Neustadt, P.C.

(57) ABSTRACT

A resin composition for denture is provided, which does not require operations for weighing, and mixing during the use; is free from involving of air bubbles; and when used for preparation of a denture base, is free from a reduction in physical properties and staining or discoloration with a lapse of time. Further, a completed denture has a high elastic energy value, is superior in impact resistance, and when applied with an impact or a stress as in the case of dropping, is not readily broken. The resin composition for denture base is in a one-paste state and is constructed by (a) a polymerizable monomer and/or oligomer having a modulus of elasticity at polymerization of 0.25 to 3.00 GPa, (b) an organic filler and/or an organic-inorganic composite filler having a modulus of elasticity of 0.25 to 3.00 GPa, and (c) a polymerization initiator made of a heat polymerization type polymerization initiator and/or a photopolymerization type polymerization initiator, and optionally, (d) an inorganic filler.

20 Claims, No Drawings

RESIN COMPOSITION FOR DENTURE BASE

BACKGROUND OF THE INVENTION

1. Field of the Invention

The present invention relates to a resin composition for denture base that is used for preparation of a denture base or a denture base plate, mending or repair of a denture, and the like. In particular, the present invention relates to a resin composition for denture base comprising a combination of a monomer component for forming a matrix after curing and a filler component.

2. Description of the Conventional Art

Hitherto, resin compositions for denture base have been consisted of a powder component made of polymethyl methacrylate or polyethyl methacrylate as a major component with a polymerization catalyst added thereto and a liquid component made of methyl methacrylate as a major component. During the use, predetermined amounts of the powder component and the liquid component are mixed with each other, and then used.

The preparation of a denture is usually carried out in the following manner. That is, an impression in an oral cavity of a patient is taken, and a gypsum cast is prepared; a denture base portion is formed by using a dental wax, etc. on the gypsum cast; the gypsum cast is set on an articulator; artificial teeth are aligned to prepare a wax denture; the wax denture is invested directly in a flask by using a gypsum investment; the wax portion is eliminated with hot water, etc., thereby forming a space for the denture base portion in the gypsum investment; a powder component and a liquid component for a resin material for denture base are weighed, and mixed with each other by means of a spatula, etc. to form a dough; the dough is filled in the space formed in the gypsum investment and then subjected to polymerization and curing; and after cooling the resulting material is removed from the gypsum investment, followed by trimming and polishing.

However, the completed denture is low in an elastic energy value, a feature of which is inherent to an acrylic resin, and is rigid and brittle in nature. Accordingly, such denture could not substantially absorb a force or an impact applied to a denture base and hence, involves such a defect that when dropped and applied with an impact, it was readily broken. Further, due to these natures, when excavating a denture from a gypsum investment during the preparation of the denture, a thin portion such as a side edge portion of the denture base, or a portion where a stress is concentrated, was liable to be broken. Moreover, since the conventional art resin compositions for denture base are required to mix the powder component and the liquid component with each other, they have such a defect that air bubbles are involved during the mixing. Such air bubbles induced a reduction in physical properties. Also, the air bubbles formed minute irregularities on the denture base surface after curing, causing staining or discoloration with a lapse of time.

In addition, during the preparation of the denture, the powder component and the liquid component for the resin composition for denture base are weighed, and mixed with each other by means of a spatula, etc.; and the mixed material is allowed to stand for a certain period of time; and when the resulting material has become into a doug-like state, it is filled. In such operation, the time until the mixed material has become into a dough-like state is liable to be influenced by an environment, and the dough-like state remains short, so that it greatly relies on an operator's perception and experiences. Further, not only the operation is difficult, but also an unpleasant feeling is imparted to the operator due to an odor or stimulation, and depending upon circumstances, the health of the operator was possibly injured.

SUMMARY OF THE INVENTION

Thus, the present invention is aimed to develop a resin composition for denture base in a one-paste state that is free from involving of air bubbles and from a reduction in physical properties and staining or discoloration with a lapse of time, because operations for weighing, and mixing is not required during the use. Further, a completed denture has a high elastic energy value, is superior in impact resistance, and when dropped and applied with an impact or a stress, is not readily broken.

In order to achieve the above-described aim, we, the present inventors made extensive and intensive investigations. As a result, they paid attention to the presence of a composite resin for dental restoration in a one-paste state as a dental resin material that does not require mixing, is superior in operability and can provide a stable performance. In another word, though the composite resin for dental restoration in a one-paste state uses an acrylic resin similar to a resin composition for denture base, since it is aimed to restore a tooth crown, an importance is attached to its hardness, bending strength and abrasion resistance. Accordingly, the composite resin for dental restoration in a one-paste state is a rigid and brittle material having a large amount of an inorganic filler or an organic-inorganic composite filler compounded therewith. Then, the inventors measured moduli of elasticity of the inorganic filler and the organic-inorganic composite filler compounded in the composite resin for dental restoration in a one-paste state and of a cured material. As a result, it has been found that the inorganic filler has a modulus of elasticity of about 5.00 GPa or more, the organic-inorganic composite filler has a modulus of elasticity of about 4.00 GPa or more, and consequently, the cured material has a modulus of elasticity of about 5.00 GPa or more. That is, it has been found that the compounding of a filler having a high modulus of elasticity ensures the hardness, bending strength and abrasion resistance of the cured material.

Thus, according to the present invention, a filler having a properly low modulus of elasticity is combined with a monomer, thereby suppressing a modulus of elasticity of a cured material to a properly low level, to complete a resin composition for denture base having a high elastic energy value so as to absorb an impact as well as being in a one-paste state without need of mixing, which is superior in operability and is free from involving of air bubbles and from a reduction in physical properties and staining or discoloration with a lapse of time.

Specifically, the resin composition for denture base according to the present invention is a resin composition for denture base in a one-paste state, comprising (a) a polymerizable monomer and/or oligomer having a modulus of elasticity at polymerization of 0.25 to 3.00 GPa, (b) an organic filler and/or an organic-inorganic composite filler having a modulus of elasticity of 0.25 to 3.00 GPa, and (c) a polymerization initiator comprising a heat polymerization type polymerization initiator and/or a photopolymerization type polymerization initiator. Of these, is preferred a resin composition for denture base in which a compounding amount of the organic filler and/or the organic-inorganic composite filler having a modulus of elasticity of 0.25 to 3.00 GPa is 1 to 75% by weight; a compounding amount of the polymerizable monomer and/or oligomer having a modulus of elasticity at polymerization of 0.25 to 3.00 GPa is from 15 to 95% by weight; and a compounding amount of the polymerization initiator comprising a heat polymerization type polymerization initiator and/or a photopolymerization type polymerization initiator is 0.05 to 5% by weight, and which may further contain from 1 to 60% by weight of an inorganic filler.

DESCRIPTION OF THE PREFERRED EMBODIMENTS

The respective components of the resin composition for denture base according to the present invention will be described below in detail.

The polymerizable monomer and/or oligomer having a modulus of elasticity at polymerization of 0.25 to 3.00 GPa as the component (a) is a component for constituting a matrix portion after curing, and monomers of a methacrylate or an acrylate having at least one unsaturated double bond are preferably used. Specific examples include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritoltetramethacrylate, polybutyleneglycol dimethacrylate, and corresponding acrylates thereto. Examples of monomers having a urethane bond include di-2-methacryloxyethyl-2,2,4-trimethylhexamethylene dicarbamate, 1,3,5-tris-[1,3-bis(methacryloyloxy)-2-propoxycarbonylaminohex ane]-1,3,5-(1H,3H,5H)triazin-2,4,6-trione, and corresponding acrylates thereto. Besides, are enumerated a urethane oligomer synthesized of 2,2'-di(4-hydroxycyclohexyl)propane, 2-oxepanone, hexamethylene diisocyanate, and 2-hydroxyethyl methacrylate and a urethane oligomer synthesized of 2,2'-di(4-hydroxycyclohexyl)propane, 2-oxepanone, hexamethylene diisocyanate, and 2-hydroxyethyl acrylate, a urethane oligomer synthesized of 1,3-butanediol, hexamethylene diisocyanate, and 2-hydroxyethyl methacrylate, and a urethane oligoner synthesized of 1,3-butanediol, hexamethylene diisocyanate, and 2-hydroxyethyl acrylate. These monomers and/or olgiomers can be used singly or in admixture, while being adjusted so as to have a modulus of elasticity of 0.25 to 3.00 GPa.

Of these polymerizable monomers and/or oligomers, neopentyl glycol dimethacrylate, tetrahydrofurfuryl methacrylate, 1,4-butanediol dimethacrylate, 1,6-hexanediol dimethacrylate, polybutylene glycol dimethacrylate, di-2-methacryloxyethyl-2,2,4-trimethylhexamethylene dicarbamate, 1,3,5-tris[1,3-bis(methacryloyloxy)-2-propoxy-carbonylamino-hexane]-1,3,5-(1H,3H,5H)triazin-2,4,6-trione, and corresponding acrylates thereto, as well as a urethane oligomer synthesized of 2,2'-di(4-hydroxycyclohexyl)propane, 2-oxepanone, hexamethylene diisocyanate, and 2-hydroxyethyl methacrylate and a urethane oligomer synthesized of 2,2'-di(4-hydroxycyclohexyl) propane, 2-oxepanone, hexamethylene diisocyanate, and 2-hydroxyethyl acrylate, a urethane oligomer synthesized of 1,3-butanediol, hexamethylene diisocyanate, and 2-hydroxyethyl methacrylate, and a urethane oligomer synthesized of 1,3-butanediol, hexamethylene diisocyanate, and 2-hydroxyethyl acrylate have a modulus of elasticity of 0.25 to 3.00 GPa after curing, even when used singly. When these monomers and/or oligomers are used singly or in combination, it is not necessary to adjust the modulus of elasticity, whereby a more suitable resin composition for denture base in a one-paste state can be obtained. Thus, such is preferred.

In the case where the modulus of elasticity of the polymerizable monomer and/or oligomer as the component (a) is less than 0.25 GPa, a matrix of the cured material is so soft that the denture is liable to be deformed. On the other hand, in the case where the modulus of elasticity of the polymerizable monomer and/or oligomer as the component (a) exceeds 3.00 GPa, the elastic energy of the cured material is so low that the denture is rigid and brittle. Thus, such is not proper. A suitable amount of the polymerizable monomer and/or oligomer as the component (a) to be compounded is preferably 15 to 95% by weight in the resin composition for denture base. When the compounding amount of the component (a) is less than 15% by weight, the cured material is liable to be inferior in strength and elasticity. On the other hand, when it exceeds 95% by weight, the cured material is liable to be sticky. An amount of 30 to 80% by weight is particularly preferred.

The organic filler and/or the organic-inorganic composite filler having a modulus of elasticity of 0.25 to 3.00 GPa as the component (b) is a component for imparting a bending strength and an elastic energy to the cured material and for ensuring an impact resistance and having a function to adjust the paste state of the resin composition for denture base. When the modulus of elasticity of the component (b) is less than 0.25 GPa, the bending strength of the cured material is insufficient. On the other hand, when it exceeds 3.00 GPa, the cured material is too rigid for application for denture base, and hence, such is not proper.

As the organic filler having a modulus of elasticity of 0.25 to 3.00 GPa, is used a powder prepared by polymerizing curing and then grinding the same substance as that used for the above-described polymerizable monomer and/or oligomer having a modulus of elasticity at polymerization of 0.25 to 3.00 GPa. As the polymerization initiator for polymerizing and curing the polymerizable monomer and/or oligomer, are usable known polymerization initiators that are generally used during the preparation of organic fillers. In the case of heat curing, heat polymerization type polymerization initiators such as organic peroxides and azo compounds are used. In the case of photopolymerization, photopolymerization type polymerization initiators are used. In addition, the polymerizable monomer and/or oligomer may be cured by autopolymerization, and there are no restrictions on the curing method.

As the organic-inorganic composite filler having a modulus of elasticity of 0.25 to 3.00 GPa, can be used those prepared by mixing the above-described polymerizable monomer and/or oligomer having a modulus of elasticity at polymerization of 0.25 to 3.00 GPa with an inorganic filler, polymerizing and curing the mixture, and then grinding the cured material. In order to adjust the modulus of elasticity at 0.25 to 3.00 GPa, such can be effected by adjusting a mixing ratio of the polymerizable monomer and/or oligomer to the inorganic filler. Examples of the inorganic filler to be mixed include various glasses such as barium glass, alumina glass, and potassium glass; and powders such as silica, feldspar, quartz, synthetic zeolite, calcium phosphate, aluminum silicate, calcium silicate, and magnesium carbonate. It is desired that these inorganic fillers are subjected to a surface processing with a silane substance in advance. As a surface processing agent that is used for the surface processing, are used organosilicon compounds such as γ-methacryloxypropyl trimethoxysilane, vinyl trichlorosilane, vinyl triethoxysilane, vinyl trimethoxysilane, vinyl triacetoxysilane, and vinyl tri (methoxyethoxy) silane. The surface processing is carried out by a known silane processing method. As the polymerization initiator for polymerizing and curing the mixture of the polymerizable monomer and/or oligomer and the inorganic filler, are used known polymerization initiators same as those used for the preparation of the organic filler as described above. A suitable amount of the inorganic filler to be compounded in the organic-inorganic composite filler is 5 to 50% by weight similar to the hitherto known organic-inorganic composite fillers.

An amount of the organic filler and/or the organic-inorganic composite filler having a modulus of elasticity of 0.25 to 3.00 GPa as the component (b) is preferably 1 to 75% by weight in the resin composition for denture base. When the amount of the component (b) is less than 1% by weight, no effect by the compounding is observed. On the other hand, when it exceeds 75% by weight, the paste becomes hard, whereby the operability tends to be lowered.

A suitable amount of the polymerization initiator comprising a heat polymerization type polymerization initiator and/or a photopolymerization type polymerization initiator as the component (c) is 0.01 to 5% by weight. When the amount of the component (c) is less than 0.01% by weight, it is difficult to carry out the polymerization and curing sufficiently as the resin composition for denture base. On the other hand, when it exceeds 5% by weight, the stable preservability of the resin composition for denture base is possibly hindered.

As the heat polymerization type polymerization initiator, are mainly used organic peroxides, azo compounds, and the like. As the organic peroxides, are preferred diacyl peroxides having an aromatic ring and peroxy esters considered to be esters of perbenzoic acid. Examples include benzoyl peroxide, 2,4-dichlorobenzoyl peroxide, m-tolyl peroxide, t-butyl peroxybenzoate, di-t-butyl peroxyisophthalate, and 2,5-dimethyl-2,5-di(benzoylperoxy)hexane. As the azo compounds, is useful azobisisobutyronitrile. In addition, organometallic compounds such as tributylboron can be used.

As the photopolymerization type polymerization initiator, are used photopolymerization initiators that can polymerize the resin composition for denture base by the action with visible rays having a wavelength of 390 to 830 nm. As the photopolymerization type polymerization initiator, is usually used a combination of a sensitizer with a reducing agent. Examples of the sensitizer include camphorquinone, benzil, diacetyl, benzyl dimethyl ketal, benzyl diethyl ketal, benzyl di(2-methoxyethyl) ketal, 4,4'-dimethybenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropyl-thioxanthone, 2-chloro-7-trifluoromethylthioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,4'-bisdiethylaminobenzophenone, and acyl phosphine oxide derivatives, and azide group-containing compounds. These sensitizers can be used singly or in admixture.

As the reducing agent, are generally employed tertiary amines. As the tertiary amines, are preferred N,N-dimethyl-p-toluidine, N,N-dimethyl-aminoethyl methacrylate, triethanolamine, methyl 4-dimethylaminobenzoate, ethyl 4-dimethylamino-benzoate, and isoamyl 4-dimethylaminobenzoate. As other reducing agents, are enumerated benzoyl peroxide, sodium sulfinate derivatives, organometallic compounds, and the like.

In addition, in the resin composition for denture base according to the present invention, so far as the characteristics of having a high elastic energy for absorbing the impact are not deteriorated, if desired, it is possible to compound an inorganic filler as a compound (d) for the purposes of adjusting the hardness or abrasion resistance and adjusting the paste viscosity. As the inorganic filler, are usable the same substances as those described above for the inorganic filler of the organic-inorganic composite filler. It is desired that the inorganic filler is similarly subjected to silane processing in advance. Incidentally, in this inorganic filler as the component (d), it is not necessary that its modulus of elasticity is limited to 0.25 to 3.00 GPa. In order to impart the hardness or abrasion resistance, it is proper to use an inorganic filler having a modulus of elasticity exceeding 3.00GPa. Preferably, an amount of the component (d) to be compounded is 1 to 60% by weight to the resin composition for denture base. When the amount of the component (d) to be compounded is less than 1% by weight, no effect by the compounding is observed. On the other hand, when it exceeds 60% by weight, the elastic energy becomes low, and hence, such is not proper.

As a matter of course, may be additionally added known polymerization inhibitors, ultraviolet light absorbers, plasticizers, coloring agents, pigments, antioxidants, discoloration preventives, surfactants, fungicides, etc.

In the case where the resin composition for denture base according to the present invention is provided as a product, depending upon the purpose, it is provided after being adjusted in a one-paste state. Namely, in the case where it is aimed to use it for the preparation of a denture of the conventional art, it is proper that the resin composition for denture base is provided in a dough-like pasty state so as to fill it into a space within gypsum investment. On the other hand, in the case where it is aimed to prepare a denture on a gypsum cast directly without preparing a wax denture, it is proper to provide a combination of the case where for the formation of a denture base portion, the resin composition does not substantially have spontaneous fluidity in a stationary state; easily flows when applied with a force but does not flow excessively; exhibits a dough-like or clay-like state such that it can easily impart a form by fingers, etc.; and is provided in a shape of a square pillar, rod, sphere, horseshoe or sheet, with the case where for the minute adjustment such as adjustment of a gap site to a cervix or and an artificial tooth or teeth, the resin composition is provided in a gel state such that it spontaneously flows slightly or exhibits slight fluidity in a stationary state. The adjustment of the fluidity in a one-paste state is usually carried out by changing the amount of the filler to be compounded.

The method for preparing a denture directly on a gypsum cast using the resin composition for denture base according to the present invention is carried out in the following manner. That is, first of all, an impression in an oral cavity is taken, and a gypsum cast is then prepared based on the thus taken impression; a denture base portion is formed on the gypsum cast using the resin composition for denture base according to the present invention; the gypsum cast is set on an articulator; artificial teeth are aligned; a form is roughly imparted; and using the pasty resin composition for denture base having fluidity, a gap site to the cervix or the artificial tooth or teeth is subjected to filling and auxiliary mending or repair, thereby imparting a final form. Thereafter, the resin composition for denture base is polymerized and cured, and then finally subjected to formation of triming and polishing, thereby completing a denture.

Incidentally, the resin composition for denture base according to the present invention can be used for various applications other than the preparation of a denture, such as preparation of a base plate, mending or repair of a denture, a temporary prosthesis, and a restorative, by applying such characteristics that it has a proper hardness and toughness and that even when applied with an impact or a stress, it is not easily broken.

Next, the invention will be described below in detail with reference to the following Examples, but it should not be construed that the invention is limited thereto.

EXAMPLE 1
Component (a): (Modulus of 48.9% by Weight Elasticity: 2.1 GPa)

| | |
|---|---|
| Tetrahydrofurfuryl methacrylate | 4% by weight |
| Polybutylene glycol dimethacrylate | 4% by weight |
| Di-2-methacryloxyethyl-2,2,4-trimethyl-hexamethylene dicarbamate | 64% by weight |
| Urethane oligomer synthesized of 2,2'-di(4-hydroxycyclohexyl)propane, 2-oxepanone, hexamethylene diisocyanate, and 2-hydroxyethyl methacrylate | 28% by weight |
| Component (b): Organic filler (modulus of elasticity: 2.1 GPa) | 50% by weight |
| Tetrahydrofurfuryl methacrylate | 4% by weight |
| Polybutylene glycol dimethacrylate | 4% by weight |
| Di-2-methacryloxyethyl-2,2,4-trimethyl-hexamethylene dicarbamate | 63% by weight |
| Urethane oligomer synthesized of 2,2'-di(4-hydroxycyclohexyl)propane, 2-oxepanone, hexamethylene diisocyanate, and 2-hydroxyethyl methacrylate | 28% by weight |
| Azobisisobutyronitrile | 1% by weight |

The above-described composition was subjected to heat polymerization and then ground to prepare an organic filler having a mean particle size of 100 μm.
Component (c):

| | |
|---|---|
| Camphorquinone | 0.5% by weight |
| Ethyl 4-dimethylaminobenzoate (Polymerization inhibitor) | 0.5% by weight |
| 6-tert-butyl-2,4-xylenol | 0.1% by weight |

The respective components were weighed, mixed and then subjected to deaeration to prepare a pasty resin composition for denture base. The various characteristic values of thus obtained resin composition for denture base were measured for bending strength, modulus of elasticity, elastic energy, and impact strength in the manners as described later. The results obtained are summarized and shown in Table 1.

Also, a denture was prepared actually by using this pasty resin composition for denture base. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

(Bending Strength, Modulus of Elasticity, and Elastic Energy)

The resin composition for denture base was pressed into a mold having a size of 2 mm×2 mm×25 mm by using a glass sheet via Cellophane, both surfaces of which were then irradiated with light for 5 minutes by means of a visible light irradiator (a trade name: LABOLIGHT LV-II, manufactured by GC Corporation), thereby effecting polymerization and curing. The thus obtained sample was immersed in water for 24 hours and then subjected to a three-point bending test at a span of 20 mm and at a cross head speed of 1 mm/min. by means of a universal testing machine (a trade name: Autograph, manufactured by Shimadzu Corporation). The number of the test samples was five. The bending strength was obtained from a maximum stress, the modulus of elasticity from a tangent line of a stress-strain curve of the chart, and the elastic energy from an area of a stress-strain curve of the chart, respectively. From the obtained values were calculated average values.

(Dynstat Impact Strength)

The resin composition for denture base was filled in a silicone mold having a size of 3 mm×10 mm×15 mm and irradiated with light for 5 minutes by means of avisible light irradiator (a trade name: LABOLIGHT LV-II, manufactured by GC Corporation). The resin composition for denture base was taken out from the mold, both surfaces of which were then irradiated with light for 5 minutes, thereby effecting polymerization and curing. The thus obtained sample was subjected to a test for Dynstat impact strength at a lifting angle of 90° and a hammer energy of 10 kg-cm by means of a Dynstat impact testing machine (manufactured by Toyo Seiki Seisaku-Sho, Ltd.). The impact strength was obtained from the measured impact value.

EXAMPLE 2

| | |
|---|---|
| Component (a): (modulus of elasticity: 1.8 GPa) | 78.9% by weight |
| Tetrahydrofurfuryl methacrylate | 6% by weight |
| Polybutylene glycol dimethacrylate | 6% by weight |
| Di-2-methacryloxyethyl-2,2,4-trimethyl-hexamethylene dicarbamate | 58% by weight |
| Urethane oligomer synthesized of 2,2'-di(4-hydroxycyclohexyl)propane, 2-oxepanone, hexamethylene diisocyanate, and 2-hydroxyethyl methacrylate | 30% by weight |
| Component (b): Organic filler (modulus of elasticity: 2.1 GPa) | 20% by weight |
| Tetrahydrofurfuryl methacrylate | 4% by weight |
| Polybutylene glycol dimethacrylate | 4% by weight |
| Di-2-methacryloxyethyl-2,2,4-trimethyl-hexamethylene dicarbamate | 63% by weight |
| Urethane oligomer synthesized of 2,2'-di(4-hydroxycyclohexyl)propane, 2-oxepanone, hexamethylene diisocyanate, and 2-hydroxyethyl methacrylate | 28% by weight |
| Azobisisobutyronitrile | 1% by weight |

The above-described composition was subjected to heat polymerization and then ground to prepare an organic filler having a mean particle size of 100 μm.

Component (c):

| | |
|---|---|
| Camphorquinone | 0.5% by weight |
| Ethyl 4-dimethylaminobenzoate | 0.5% by weight |
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1.

Also, using this pasty resin composition for denture base, a denture was prepared in the same manner as in Example 1. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

EXAMPLE 3

| | |
|---|---|
| Component (a): (modulus of elasticity: 1.4 GPa) | 48.9% by weight |
| Neopentyl glycol dimethacrylate | 4% by weight |
| Polybutylene glycol dimethacrylate | 4% by weight |
| Di-2-methacryloxyethyl-2,2,4-trimethyl-hexamethylene dicarbamate | 50% by weight |
| Urethane oligomer synthesized of 2,2'-di(4-hydroxycyclohexyl)propane, 2-oxepanone, hexamethylene diisocyanate, and 2-hydroxyethyl acrylate | 42% by weight |
| Component (b): Organic-inorganic composite filler (modulus of elasticity: 2.5 GPa) | 50% by weight |
| Component (a) as described above | 69.5% by weight |
| Azobisisobutyronitrile | 0.5% by weight |
| Ultrafine silica | 30% by weight |

The mixture comprising the above-described components was subjected to heat polymerization for curing and then ground to prepare an organic-inorganic composite filler having a mean particle size of 120 μm.

Component (c):

| | |
|---|---|
| Camphorquinone | 0.5% by weight |
| Ethyl 4-dimethylaminobenzoate | 0.5% by weight |
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1.

Also, using this pasty resin composition for denture base, a denture was prepared in the same manner as in Example 1. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

EXAMPLE 4

| | |
|---|---|
| Component (a): (modulus of elasticity: 1.4 GPa) | 48.9% by weight |
| Tetrahydrofurfuryl methacrylate | 6% by weight |
| Polybutylene glycol dimethacrylate | 4% by weight |
| Di-2-methacryloxyethyl-2,2,4-trimethyl-hexamethylene dicarbamate | 50% by weight |
| Urethane oligomer synthesized of 2,2'-di(4-hydroxycyclohexyl)propane, 2-oxepanone, hexamethylene diisocyanate, and 2-hydroxyethyl acrylate | 40% by weight |
| Component (b): Organic-inorganic composite filler (modulus of elasticity: 1.8 GPa) | 40% by weight |
| Polybutylene glycol dimethacrylate | 4% by weight |
| Di-2-methacryloxyethyl-2,2,4-trimethyl-hexamethylene dicarbamate | 41.5% by weight |
| Urethane oligomer synthesized of 2,2'-di(4-hydroxycyclohexyl)propane, 2-oxepanone, hexamethylene diisocyanate, and 2-hydroxyethyl acrylate | 39% by weight |
| Azobisisobutyronitrile | 0.5% by weight |
| Powdered quartz subjected to surface processing with vinyl trichlorosilane | 15% by weight |

The mixture comprising the above-described components was subjected to heat polymerization for curing and then ground to prepare an organic-inorganic composite filler having a mean particle size of 120 μm.

Component (c):

| | |
|---|---|
| Camphorquinone | 0.5% by weight |
| Ethyl 4-dimethylaminobenzoate | 0.5% by weight |
| Component (d): | |
| Powdered quartz subjected to surface processing with vinyl trichlorosilane (modulus of elasticity: 95 GPa) | 10% by weight |
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1.

Also, using this pasty resin composition for denture base, a denture was prepared in the same manner as in Example 1. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

EXAMPLE 5

| | |
|---|---|
| Component (a): (modulus of elasticity: 0.7 GPa) | 39.75% by weight |
| Polybutylene glycol dimethacrylate | 20% by weight |
| Di-2-methacryloxyethyl-2,2,4-trimethyl-hexamethylene dicarbamate | 40% by weight |
| Urethane oligomer synthesized of 2,2'-di(4-hydroxycyclohexyl)propane, 2-oxepanone, hexamethylene diisocyanate, and 2-hydroxyethyl methacrylate | 40% by weight |
| Component (b): Organic-inorganic composite filler (modulus of elasticity: 1.5 GPa) | 40% by weight |
| Component (a) as described above | 79.5% by weight |
| Azobisisobutyronitrile | 0.5% by weight |
| Ultrafine silica | 20% by weight |

The mixture comprising the above-described components was subjected to heat polymerization for curing and then ground to prepare an organic-inorganic composite filler having a mean particle size of 120 μm.
Component (c):

| | |
|---|---|
| Benzoyl peroxide | 0.15% by weight |
| Component (d): | |
| Powdered quartz subjected to surface processing with vinyl trichlorosilane (modulus of elasticity: 95 GPa) | 20% by weight |
| (Polymerization inhibitor) 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values including a bending strength, a modulus of elasticity, an elastic energy, and an impact strength were measured in the same manner as in Example 1, except that the resin composition for denture base was heated in warm water at 70° C. for 90 minutes and then in hot water at 100° C. for 30 minutes, thereby effecting polymerization and curing. The results obtained are summarized and shown in Table 1.

Also, this pasty resin composition for denture base was filled in a cavity formed in an investment within a flask, heated in warm water at 70° C. for 90 minutes, and then heated for polymerization in hot water at 100° C. for 30 minutes, to prepare a denture. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

EXAMPLE 6

| | |
|---|---|
| Component (a): (modulus of elasticity: 1.9 GPa) | 44.75% by weight |
| Neopentyl glycol dimethacrylate | 22% by weight |
| Polybutylene glycol dimethacrylate | 10% by weight |
| Di-2-methacryloxyethyl-2,2,4-trimethyl-hexamethylene dicarbamate | 46% by weight |
| Urethane oligomer synthesized of 1,3-butanediol, hexamethylene diisocyanate, and 2-hydroxyethyl methacrylate | 22% by weight |
| Component (b): Organic-inorganic composite filler (modulus of elasticity: 2.3 GPa) | 55% by weight |
| Component (a) as described above | 89.5% by weight |
| Azobisisobutyronitrile | 0.5% by weight |
| Powdered silica processed with γ-methacryloxypropyl trimethoxysilane | 10% by weight |

The mixture comprising the above-described components was subjected to heat polymerization for curing and then ground to prepare an organic-inorganic composite filler having a mean particle size of 100 μm.
Component (c):

| | |
|---|---|
| Benzoyl peroxide (Polymerization inhibitor) | 0.15% by weight |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 5. The results obtained are summarized and shown in Table 1.

Also, using this pasty resin composition for denture base, a denture was prepared in the same manner as in Example 5. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

EXAMPLE 7

| | |
|---|---|
| Component (a): (modulus of elasticity: 1.2 GPa) | 68.9% by weight |
| Urethane oligomer synthesized of 2,2'-di(4-hydroxycyclohexyl)propane, 2-oxepanone, hexamethylene diisocyanate, and 2-hydroxyethyl methacrylate | 100% by weight |
| Component (b): Organic-inorganic composite filler (modulus of elasticity: 2.6 GPa) | 30% by weight |
| Urethane oligomer synthesized of 2,2'-di(4-hydroxycyclohexyl)propane, 2-oxepanone, hexamethylene diisocyanate, and 2-hydroxyethyl methacrylate | 79% by weight |
| Powdered silica processed with γ-methacryloxypropyl trimethoxysilane | 20% by weight |
| Azobisisobutyronitrile | 1% by weight |

The above-described composition was subjected to heat polymerization and then ground to prepare an organic-inorganic composite filler having a mean particle size of 100 μm.
Component (c):

| | |
|---|---|
| Camphorquinone | 0.5% by weight |
| Ethyl 4-dimethylaminobenzoate | 0.5% by weight |

-continued

| | |
|---|---|
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1.

Also, using this pasty resin composition for denture base, a denture was prepared in the same manner as in Example 1. In this operation, since it was not required to weigh a powder and a liquid and to measure the time from mixing to formation of a dough, a series of operations were very simple. Further, a monomer odor was not substantially presented. Moreover, even when the completed denture was set for one month, were not observed discoloration, staining, and the like.

COMPARATIVE EXAMPLE 1

As the conventional art powder-liquid type resin composition for denture base, was used a resin for denture base (a trade name: GC ACRON, made by GC Corporation) According to the instructions in the specification, the powder and the liquid were weighed, and mixed with each other. Thereafter, the mixed material was allowed to stand for 30 minutes until it had become into a dough-like state. Then, the bending strength, modulus of elasticity, elastic energy and impact strength were measured in the same manner as in Example 5. The results obtained are summarized and shown in Table 1.

Further, a denture base was then prepared in the same manner as in Example 5. As a result, the operations until the material had become into a dough-like state were complicated, and an unpleasant monomer odor was presented during the operations. Therefore, it was necessary to carry out the operations while ventilation. When the completed denture base was set for one month, discoloration was observed in minute irregular portions on the surface.

COMPARATIVE EXAMPLE 2

| | |
|---|---|
| Component (a): (modulus of elasticity: 2.8 GPa) | 29.9% by weight |
| Tetrahydrofurfuryl methacrylate | 6% by weight |
| Di-2-methacryloxyethyl-2,2,4-trimethyl-hexamethylene dicarbamate | 94% by weight |
| Component (b): Organic-inorganic composite filler (modulus of elasticity: 5.4 GPa) made from | 25% by weight |
| 2,2-Bis(4-methacryloxypolyethoxy-phenyl)propane | 49% by weight |
| Triethylene glycol dimethacrylate | 20.5% by weight |
| Azoisobutyronitrile | 0.5% by weight |
| Silica | 30% by weight |

The mixture comprising the above-described components was subjected to heat polymerization for curing and then ground to prepare an organic-inorganic composite filler having a mean particle size of 100 μm.

Component (c):

| | |
|---|---|
| Camphorquinone | 0.5% by weight |
| Ethyl 4-dimethylaminobenzoate | 0.5% by weight |
| Component (d): | |
| Powdered quartz (modulus of elasticity: 95 GPa) | 20% by weight |
| Powdered silica (modulus of elasticity: 82 GPa) | 25% by weight |
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1. Further, a denture base was prepared in the same manner as in Example 1. When the thus prepared denture base was dropped, it was easily broken.

COMPARATIVE EXAMPLE 3

| | |
|---|---|
| Component (a): (modulus of elasticity: 1.8 GPa) | 78.9% by weight |
| Tetrahydrofurfuryl methacrylate | 6% by weight |
| Polybutylene glycol dimethacrylate | 6% by weight |
| Di-2-methacryloxyethyl-2,2,4-trimethyl-hexamethylene dicarbamate | 58% by weight |
| Urethane oligomer synthesized of 2,2'-di(4-hydroxycyclohexyl)propane, 2-oxepanone, hexamethylene diisocyanate, and 2-hydroxyethyl methacrylate | 30% by weight |
| Component (b): Organic-inorganic composite filler (modulus of elasticity: 5.4 GPa) made from | 20% by weight |
| 2,2-bis(4-methacryloxypolyethoxy-phenyl)propane | 49% by weight |
| Triethylene glycol dimethacrylate | 20.5% by weight |
| Azoisobutyronitrile | 0.5% by weight |
| Fine powdered silica | 30% by weight |

The mixture comprising the above-described components was subjected to heat polymerization for curing and then ground to prepare an organic-inorganic composite filler having a mean particle size of 120 μm.

Component (c):

| | |
|---|---|
| Camphorquinone | 0.5% by weight |
| Ethyl 4-dimethylaminobenzoate | 0.5% by weight |
| (Polymerization inhibitor) | |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1. Further, a denture base was prepared in the same manner as in Example 1. When the thus prepared denture base was dropped, it was easily broken.

COMPARATIVE EXAMPLE 4

| Component (a): (modulus of elasticity: 1.4 GPa) | 48.9% by weight |
|---|---|
| Neopentyl glycol dimethacrylate | 4% by weight |
| Polybutylene glycol dimethacrylate | 4% by weight |
| Di-2-methacryloxyethyl-2,2,4-trimethyl-hexamethylene dicarbamate | 50% by weight |
| Urethane oligomer synthesized of 2,2'-di(4-hydroxycyclohexyl)propane, 2-oxepanone, hexamethylene diisocyanate, and 2-hydroxyethyl methacrylate | 42% by weight |
| Component (b): Organic-inorganic composite filler (modulus of elasticity: 3.2 GPa) | 50% by weight |
| Di-2-methacryloxyethyl-2,2,4-trimethyl-hexamethylene dicarbamate | 40% by weight |
| Triethylene glycol dimethacrylate | 40% by weight |
| Azobisisobutyronitrile | 0.5% by weight |
| Ultra fine silica | 19.5% by weight |

The mixture comprising the above-described components was subjected to heat polymerization for curing and then ground to prepare an organic-inorganic composite filler having a mean particle size of 120 μm.

Component (c):

| Camphorquinone | 0.5% by weight |
|---|---|
| Ethyl 4-dimethylaminobenzoate (Polymerization inhibitor) | 0.5% by weight |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1. Further, a denture base was prepared in the same manner as in Example 1. When the thus prepared denture base was dropped, it was easily broken.

COMPARATIVE EXAMPLE 5

| Component (a): (modulus of elasticity: 0.7 GPa) | 49.75% by weight |
|---|---|
| Polybutylene glycol dimethacrylate | 20% by weight |
| Di-2-methacryloxyethyl-2,2,4-trimethyl-hexamethylene dicarbamate | 40% by weight |
| Urethane oligomer synthesized of 2,2'-di(4-hydroxycyclohexyl)propane, 2-oxepanone, hexamethylene diisocyanate, and 2-hydroxyethyl acrylate | 40% by weight |
| Component (d): | |
| Silica (modulus of elasticity: 82 GPa) | 30% by weight |
| Powdered quartz (modulus of elasticity: 95 GPa) | 20% by weight |
| Component (c): | |
| Benzoyl peroxide (Polymerization inhibitor) | 0.15% by weight |
| 6-tert-butyl-2,4-xylenol | 0.1% by weight |

The respective components were weighed, mixed and then subjected to deaeration to prepare a pasty resin composition for denture base. Using the thus obtained resin composition for denture base, various characteristic values were measured in the same manner as in Example 1. The results obtained are summarized and shown in Table 1. Further, a denture base was prepared in the same manner as in Example 1. When the thus prepared denture base was dropped, it was easily broken.

TABLE 1

| | Bending strength (MPa) | Modulus of elasticity (GPa) | Elastic energy (MPa) | Impact strength (kg · cm/cm$^2$) |
|---|---|---|---|---|
| Example 1 | 90 | 2.3 | 3.5 | 11.5 |
| Example 2 | 85 | 1.8 | 4.3 | 12.5 |
| Example 3 | 80 | 2.1 | 5.8 | 13.8 |
| Example 4 | 81 | 2.0 | 3.8 | 11.1 |
| Example 5 | 86 | 2.7 | 3.2 | 9.5 |
| Example 6 | 91 | 2.5 | 3.5 | 10.5 |
| Example 7 | 79 | 1.9 | 3.1 | 9.8 |
| Comparative Example 1 | 65 | 2.5 | 0.9 | 6.1 |
| Comparative Example 2 | 90 | 6.5 | 1.2 | 3.2 |
| Comparative Example 3 | 42 | 3.5 | 0.4 | 3.5 |
| Comparative Example 4 | 69 | 2.6 | 1.1 | 4.2 |
| Comparative Example 5 | 70 | 3.9 | 1.2 | 4.1 |

As described above in detail, the resin composition for denture base according to the present invention is in a one-paste state. Accordingly, it does not require complicated operations as in the conventional art resin compositions for denture base, in which a powder and a liquid are weighed, and mixed with each other, and the mixed mixture is allowed to stand for a certain period of time until it has become into a dough-like state. Further, since the resin composition for denture base according to the present invention is previously made pasty so as to have a viscosity similar to those in a doug-like state, it is possible to prepare a denture directly on a gypsum cast. Moreover, the resin composition for denture base according to the present invention is superior in bending strength and elastic energy characteristics, and hence, it is possible to prepare a denture having a superior impact strength such that even when applied with an impact or a stress as in the case of dropping, the denture is not readily broken. Even further, since the dough-like paste state is maintained until a heat or light has been applied, operability is extremely superior and a denture that is less in staining and discoloration by incorporation of air bubbles can be obtained. Thus, the invention is extremely valuable in contributing to the dental remedy.

While the invention has been described in detail and with reference to specific embodiments thereof, it will be apparent to one skilled in the art that various changes and modifications can be made therein without departing from the spirit and scope thereof.

What is claimed is:

1. A one-paste resin composition for denture base, comprising:
    (a) at least one of a polymerizable monomer or a polymerizable oligomer having a modulus of elasticity after polymerization of 0.25 to 3.00 GPa;
    (b) at least one of an organic filler or an organic-inorganic composite filler having a modulus of elasticity of 0.25 to 3.00 GPa; and
    (c) a polymerization initiator comprising at least one of a heat polymerization initiator or a photopolymerization initiator.

2. The resin composition for a denture base as claimed in claim 1, wherein
   a compounding amount of said polymerizable monomer or polymerizable oligomer having a modulus of elasticity after polymerization of 0.25 to 3.00 GPa is 15 to 95% by weight;
   a compounding amount of said organic filler or organic-inorganic composite filler having a modulus of elasticity of 0.25 to 3.00 GPa is 1 to 75% by weight; and
   a compounding amount of said polymerization initiator comprising at least one heat polymerization initiator or a photopolymerization initiator is 0.5 to 5.0% by weight.

3. A resin composition for denture base as claimed in claim 1, further comprising from an inorganic filler.

4. A one-paste resin composition for a denture base, comprising:
   (a) at least one of a polymerizable monomer or a polymerizable oligomer having a modulus of elasticity after polymerization of 0.25 to 3.00 GPa;
   (b) at least one of an organic filler or an organic-inorganic composite filler having a modulus of elasticity of 0.25 to 3.00 GPa; and
   (c) a polymerization initiator comprising at least one of a heat polymerization initiator or a photopolymerization initiator,
wherein said organic filler or said organic-inorganic composite filler is a powder prepared by polymerizing, curing and then grinding the same substance as used for (a), or is a powder prepared by polymerizing with an inorganic filler, curing and grinding the same substance as that used for (a).

5. The resin composition for denture base as claimed in claim 1, wherein said polymerizable monomer is a methacrylate or an acrylate.

6. The resin composition for denture base as claimed in claim 1, wherein said polymerizable monomer is a methacrylate.

7. The resin composition for denture base as claimed in claim 1, wherein said polymerizable monomer is at least one monomer selected from the group consisting of methyl methacrylate, ethyl methacrylate, isopropyl methacrylate, 2-hydroxyethyl methacrylate, 3-hydroxypropyl methacrylate, 2-hydroxy-1,3-dimethacryl-oxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritoltetramethacrylate, polybutyleneglycol dimethacrylate, di-2-methacryloxyethyl-2,2,4-trimethyl-hexamethylene dicarbamate, 1,3,5-tris-[1,3-bis(methacryloyloxy)-2-propoxycarbonylaminohexane]-1,3,5-(1H,3H,5H)triazin-2,4,6-trione, and mixtures thereof.

8. The resin composition for denture base as claimed in claim 1, wherein said polymerizable monomer is an acrylate.

9. The resin composition for denture base as claimed in claim 1, wherein said polymerizable monomer is at least one monomer selected from the group consisting of methyl acrylate, ethyl acrylate, isopropyl acrylate, 2-hydroxyethyl acrylate, 3-hydroxypropyl acrylate, 2-hydroxy-1,3-diacryloxypropane, n-butyl acrylate, isobutyl acrylate, hydroxypropyl acrylate, tetrahydrofurfuiryl acrylate, glycidyl acrylate, 2-methoxyethyl acrylate, 2-ethylhexyl acrylate, benzyl acrylate, ethylene glycol diacrylate, diethylene glycol diacrylate, triethylene glycol diacrylate, butylene glycol diacrylate, neopentyl glycol diacrylate, 1,3-butanediol diacrylate, 1,4-butanediol diacrylate, 1,6-hexanediol diacrylate, trimethylolpropane triacrylate, trimethylolethane triacrylate, pentaerythritol triacrylate, trimethylolmethane triacrylate, pentaerythritoltetraacrylate, polybutyleneglycol diacrylate, di-2-acryloxyethyl-2,2,4-trimethyl-hexamethylene dicarbamate, 1,3,5-tris-[1,3-bis(acryloyloxy)-2-propoxycarbonyl-aminohexane]-1,3,5-(1H,3H,5H)triazin-2,4,6-trione, and mixtures thereof.

10. The resin composition for denture base as claimed in claim 1, wherein said polymerizable oligomer is selected from the group consisting of a urethane oligomer synthesized from 2,2'-di(4-hydroxycyclohexyl)propane, 2-oxepanone, hexamethylene diisocyanate and 2-hydroxyethyl methacrylate; a urethane oligomer synthesized from 2,2'-di(4-hydroxycyclohexyl)propane, 2-oxepanone, hexamethylene diisocyanate and 2-hydroxyethyl acrylate; a urethane oligomer synthesized of 1,3-butanediol, hexamethylene diisocyanate and 2-hydroxyethyl methacrylate; and a urethane oligomer synthesized of 1,3-butanediol, hexamethylene diisocyanate, 2-hydroxyethyl acrylate, and mixtures thereof.

11. The resin composition for denture base as claimed in claim 1, wherein (a) is at least one polymerizable monomer.

12. The resin composition for denture base as claimed in claim 1, wherein (a) is at least one polymerizable oligomer.

13. The resin composition for denture base as claimed in claim 2, wherein said polymerizable monomer or polymerizable oligomer comprises 30–80% by weight of said resin composition.

14. The resin composition for denture base as claimed in claim 2, wherein said polymerizable monomer comprises 30–80% by weight of said resin composition.

15. The resin composition for denture base as claimed in claim 2, wherein said polymerizable oligomer comprises 30–80% by weight of said resin composition.

16. The resin composition for denture base as claimed in claim 1, wherein said organic-inorganic composite filler comprises an inorganic filler selected from the group consisting of barium glass, alumina glass, and potassium glass, silica, feldspar, quartz, synthetic zeolite, calcium phosphate, aluminum silicate, calcium silicate, magnesium carbonate, and mixtures thereof.

17. The resin composition for denture base as claimed in claim 1, wherein said polymerization initiator is a heat polymerization type polymerization initiator selected from the group consisting of benzoylperoxide, 2,4-dichlorobenzoyl peroxide, m-tolyl peroxide, t-butyl peroxybenzoate, di-t-butyl peroxyisophthalate, 2,5-dimethyl-2,5-di(benzoyl peroxy) hexane, azobisisobutyronitrile, tributylboron, and mixtures thereof.

18. The resin composition for denture base as claimed in claim 3, wherein said inorganic filler is selected from the group consisting of barium glass, alumina glass, and potassium glass, silica, feldspar, quartz, synthetic zeolite, calcium phosphate, aluminum silicate, calcium silicate, magnesium carbonate, and mixtures thereof.

19. A method of preparing a denture base which comprises forming a denture base comprising the resin composition of claim 1 on a gypsum cast.

20. A denture comprising the resin composition of claim 1.

* * * * *